(12) United States Patent
Schäfer

(10) Patent No.: US 10,251,814 B2
(45) Date of Patent: Apr. 9, 2019

(54) CEFUROXIME SAFETY DELIVERY SYSTEM

(75) Inventor: Rolf Schäfer, Arisdorf (CH)

(73) Assignee: CIS PHARMA AG, Bubendorf (CH)

( * ) Notice: Subject to any disclaimer, the term of this patent is extended or adjusted under 35 U.S.C. 154(b) by 1136 days.

(21) Appl. No.: 13/261,707

(22) PCT Filed: Feb. 14, 2012

(86) PCT No.: PCT/EP2012/052442
§ 371 (c)(1),
(2), (4) Date: Oct. 16, 2013

(87) PCT Pub. No.: WO2012/110471
PCT Pub. Date: Aug. 23, 2012

(65) Prior Publication Data
US 2014/0039386 A1   Feb. 6, 2014

(30) Foreign Application Priority Data
Feb. 15, 2011   (WO) ............... PCT/EP2011/000848

(51) Int. Cl.
| | | |
|---|---|---|
| *A61J 1/00* | (2006.01) | |
| *A61J 1/20* | (2006.01) | |
| *A61K 9/00* | (2006.01) | |
| *A61M 5/00* | (2006.01) | |
| *A61M 5/19* | (2006.01) | |
| *A61M 5/24* | (2006.01) | |
| *A61M 5/178* | (2006.01) | |
| *A61M 5/315* | (2006.01) | |
| *A61K 31/546* | (2006.01) | |
| *F16D 43/18* | (2006.01) | |

(52) U.S. Cl.
CPC ............... *A61J 1/2096* (2013.01); *A61J 1/00* (2013.01); *A61J 1/20* (2013.01); *A61J 1/2089* (2013.01); *A61K 9/0048* (2013.01); *A61K 31/546* (2013.01); *A61M 5/00* (2013.01); *A61M 5/178* (2013.01); *A61M 5/19* (2013.01); *A61M 5/2448* (2013.01); *A61M 5/31596* (2013.01); *F16D 43/18* (2013.01)

(58) Field of Classification Search
CPC .......... A61M 5/19; A61M 5/178; A61M 5/00; A61M 5/2488; A61M 25/0631; A61M 5/31596; A61J 1/20; A61J 1/2096; A61J 1/2089; A61J 1/00
See application file for complete search history.

(56) References Cited

U.S. PATENT DOCUMENTS

| | | | |
|---|---|---|---|
| 3,327,710 A | 6/1967 | de Santo et al. | |
| 3,380,451 A | 4/1968 | Porter et al. | |
| 4,522,302 A * | 6/1985 | Paikoff .................. | A61B 50/33 206/216 |
| 4,581,016 A | 4/1986 | Gettig | |
| 5,637,087 A | 6/1997 | O'Neil et al. | |
| 5,716,338 A | 2/1998 | Hjertman et al. | |
| 5,779,668 A | 7/1998 | Grabenkort | |
| 5,785,683 A | 7/1998 | Szapiro et al. | |
| 6,238,372 B1 * | 5/2001 | Zinger .................. | A61J 1/2089 604/246 |
| 6,478,771 B1 | 11/2002 | Lavi et al. | |
| 8,535,276 B2 | 9/2013 | Salzman | |
| 8,641,661 B2 * | 2/2014 | Delmotte .............. | A61J 1/2096 604/416 |
| 2002/0087144 A1 | 7/2002 | Zinger | |
| 2003/0040701 A1 | 2/2003 | Dalmose | |
| 2004/0247628 A1 | 12/2004 | Lintz | |
| 2005/0215957 A1 * | 9/2005 | Hynes ............... | A61M 5/31551 604/218 |
| 2007/0208295 A1 | 9/2007 | Oloodmiyazdi | |
| 2009/0118669 A1 | 5/2009 | Bendek | |
| 2011/0054437 A1 * | 3/2011 | Perovitch ............. | A61J 1/2093 604/411 |
| 2012/0029464 A1 | 2/2012 | Kragelund et al. | |

(Continued)

FOREIGN PATENT DOCUMENTS

| | | |
|---|---|---|
| JP | 2010 200198 | 9/2010 |
| WO | WO2007 130061 | 11/2007 |
| WO | WO2006 058061 | 6/2008 |

(Continued)

OTHER PUBLICATIONS

"Cefuroxlm: 100-10 108". In: Bundesverband der Pharmazeutischen Industrie: "Rote Lisle 2003", Jan. 1, 2003 (Jan. 1, 2003), Rote Lisle Service GmBH, Frankfurt/Main, XP002663948 ISBN: 3-87193-26B-X, abstract.

(Continued)

*Primary Examiner* — Theodore J Stigell
(74) *Attorney, Agent, or Firm* — Richard Voellmy

(57) ABSTRACT

The present invention relates to safety delivery systems for intracameral administration of an appropriate dose of cefuroxime subsequent to cataract and other eye surgery. A preferred embodiment of an cefuroxime safety delivery system according to the invention comprises (a) a perforable sterile vial sterile-filled with a measured amount of cefuroxime, (b) a reconstitution syringe with a male luer fitting sterile-filled with 0.1 ml of isotonic salt solution per mg cefuroxime in the perforable vial and a vial adapter with a female luer fitting or one or more needles with female luer fitting, and (c) one or more sterilized delivery syringes with male luer fitting, each delivery syringe being capable of holding at least 0.1 ml of ejectable liquid and containing a marking indicating a fill volume of 0.1 ml of ejectable liquid.

21 Claims, No Drawings

(56) References Cited

U.S. PATENT DOCUMENTS

2013/0053814 A1     2/2013    Mueller-Beckhaus et al.
2014/0081238 A1     3/2014    Bendek

FOREIGN PATENT DOCUMENTS

WO    WO2010 043685     4/2010
WO    WO2012 021088     2/2012

OTHER PUBLICATIONS

"Caverject 10micro g/-20 micro g: 82 216".In: Bundesverband der Pharmazeutischen Industrie: "Rote Liste 2003", Jan. 1, 2003 (Jan. 1, 2003), Rote Liste Service GmBH, Frankfurt/Main, XP002663949, ISBN: 3-87193-288-X, abstract.

Yorsten, D. (2008) Using intrecameral cefuroxime as a prophylaxis for endophthalmitis. Community Eye Health Journal, vol. 21, Issue 65.

"Cefuroxim: 100-10 106". In: Bundesverband der Pharmazeutischen Industrie: "Rote Liste 2003", Jan. 1, 2003 (Jan. 1, 2003), Rote Liste Service GmBH, Frankfurt/Main, XP002663948 ISBN: 3-87193-268-X, abstract.

"Caverject 10micro g/-20 micro g: 82 216".In: Bundesverband der Pharmazeutischen Industrie: "Rote Liste 2003", Jan. 1, 2003 (Jan. 1, 2003), Rote Liste Service GmBH, Frankfurt/Main, XP002663949, ISBN: 3-87193-268-X, abstract.

Yorsten, D. (2008) Using intracameral cefuroxime as a prophylaxis for endophthalmitis. Community Eye Health Journal, vol. 21, issue 65.

Yu-Wai-Man et al. (2008) Efficacy of intracameral and subconjunctival cefuroxime in preventing endophthalmititis after cataract surgery. J Cataract Refract Surg 34: 447-51.

\* cited by examiner

CEFUROXIME SAFETY DELIVERY SYSTEM

The present application is a national phase of international patent application PCT/EP2012/052442 designating the United States, filed on Feb. 14, 2012, which international application claims priority from international patent application PCT/EP2011/000848, filed on Feb. 15, 2011.

FIELD OF THE INVENTION

The invention relates to delivery systems useful for safe intracameral injection of a precise dose of cefuroxime in patients undergoing ophthalmic surgeries such as cataract surgery.

BACKGROUND OF THE INVENTION

Postoperative endophthalmitis is a feared albeit relatively rare complication of cataract surgery. The incidences reported in the two large studies discussed below were 0.06 and 0.17%, respectively. Infection by bacteria, primarily staphylococci and streptococci, can lead to legal blindness.

A large study was conducted in Sweden that involved 188,155 patients and addressed the question of the benefit of intracameral injection of antibiotics during cataract surgery. Wejde et al 2005 Acta Ophthalmol Scand 83: 7-10. The results of the study revealed a reduction of endophthalmitis by a factor of greater than 4 in patients that had received intracameral antibiotic. In 98.5% of cases, the antibiotic used was cefuroxime, which antibiotic is active against gram-positive bacteria. The remaining 1.5% received gentamycin and vancomycin. Gram-positive bacteria were the dominating aetiology in the endophthalmitis cases observed (84.6% proven by culture).

Results of a large study of the European Society of Cataract & Refractive Surgeons (ESCRS) were reported in 2007. J Cataract Refract Surg 33: 978-88. The study was carried out at 24 centers in 9 European countries and included 16,603 patients that underwent phacoemulsification cataract surgery with placement of an intraocular lens. The patients were assigned to four groups. Group A received no antibiotic prophylaxis. Group B received intracameral cefuroxime (1 mg in 0.1 ml of normal saline) at the end of surgery. Group C was administered levofloxacin drops prior and subsequent to surgery. Group D received both cefuroxime and levofloxacin. Twenty-nine patients experienced endophthalmitis. The study revealed that injection of cefuroxime reduced the risk for endophthalmitis by nearly five fold. Levofloxacin drops were essentially without effect.

These studies unambiguously demonstrated the considerable benefit of intracameral injection of cefuroxime. Although cefuroxime has been used widely in ophthalmic practice for about ten years, there are still no formulations and delivery systems available that were specifically designed or assembled for ophthalmic use. Cefuroxime has limited stability in aqueous solution, in which it hydrolyses at a rate of about 10% in 48 hours (at room temperature). Hence, practitioners currently have to purchase the drug as a bulk powder and have to dissolve and dilute the resulting solution down to the concentration appropriate for prompt intracameral injection. The above-mentioned ESCRS study followed a protocol comprising 16 individual steps for preparing an intracameral injection of cefuroxime. This "kitchen pharmacy" approach is highly inconvenient and time-consuming considering that the cataract procedure itself takes only about 7.5 minutes.

SUMMARY OF THE INVENTION

The subject invention relates to cefuroxime safety delivery systems for facilitating injection of the antibiotic cefuroxime into the anterior chamber of the eye during or after cataract surgery or other surgical intervention in the anterior part of the eye or into the posterior chamber during or after surgical intervention in the posterior part of the eye.

In general, a cefuroxime safety delivery system of the invention comprises (1) a perforable sterile vial sterile-filled with a measured amount of cefuroxime, (2) a receptacle holding 0.1 ml of sterile isotonic salt solution per mg cefuroxime in the perforable vial and means for transferring the isotonic salt solution to the perforable vial and for removing from the perforable vial an aliquot of cefuroxime dissolved in the isotonic salt solution into a delivery syringe, and (3) one or more sterilized delivery syringes with male luer fitting, each delivery syringe being capable of holding at least 0.1 ml of ejectable liquid and containing a marking indicating a fill volume of 0.1 ml of ejectable liquid. Hence, a delivery syringe filled to the 0.1 ml mark will eject through its tip a volume of 0.1 ml when the plunger is pushed to its forward-most position. To remove fine particles from the cefuroxime solution prior to injection into the eye of a patient, a sterile filter with a pore size of 0.2 µm can be interposed between delivery syringe and injection needle. If such a filter is to be used, there may be a need for repositioning the 0.1 ml mark on the delivery syringe such that any volume of liquid lost in the filter is compensated. Suitable sterile filters that contain a female luer fitting on the inlet side and a male luer fitting on the outlet side can be obtained from several sources. An example filter is Puradisc4 from Whatman, GE Healthcare. It is noted that certain components of the delivery systems of the invention including perforable vials and syringes typically comprise removable protective coverings.

In particular embodiments, the cefuroxime safety delivery system invention comprises (1) a perforable sterile vial sterile-filled with a measured amount of cefuroxime, (2) a sterile-filled reconstitution syringe with male luer fitting holding 0.1 ml of sterile isotonic salt solution per mg cefuroxime in the perforable vial and a vial adapter with female luer fitting or one or more shield-protected needles with female luer fitting, and (3) one or more sterilized delivery syringes with male luer fitting, each delivery syringe being capable of holding at least 0.1 ml of ejectable liquid and containing a marking indicating a fill volume of 0.1 ml of ejectable liquid. The vial adapter preferably is a swabable multidose adapter in systems designed for withdrawal of multiple cefuroxime doses or a vented vial adapter in single-dose systems.

In another particular embodiment, the cefuroxime safety delivery system invention comprises (1) a perforable sterile vial sterile-filled with a measured amount of cefuroxime, (2) a sterile-filled reconstitution syringe with male luer fitting holding 0.1 ml of sterile isotonic salt solution per mg cefuroxime in the perforable vial and a flow control device, and (3) a sterilized delivery syringe with male luer fitting capable of holding at least 0.1 ml of ejectable liquid and containing a marking indicating a fill volume of 0.1 ml of ejectable liquid.

The subject invention also relates to the use of the latter particular cefuroxime safety delivery systems for the preparation of one mg doses of cefuroxime for intracameral injection. Preparation of the latter doses comprises the steps of (1) transferring the entire contents of the prefilled reconstitution syringe into the perforable vial comprising cefuroxime, (2) manually shaking said vial to obtain a homogeneous solution of the contents of the closed vial, and (3) withdrawing into the delivery syringe 0.1 ml of ejectable solution from said vial.

Another particular embodiment relates to a cefuroxime safety delivery system that comprises (1) a first perforable sterile vial sterile-filled with a measured amount of cefuroxime, (2) a second perforable vial sterile-filled with 0.1 ml of sterile isotonic salt solution per mg cefuroxime in the first perforable vial, an empty reconstitution syringe with a male luer fitting and a fill volume sufficiently large to hold the isotonic salt solution contained in the second perforable vial and two vial adapters with female luer fitting or one or more shield-protected needles with female luer fitting, and (3) one or more sterilized delivery syringes with male luer fitting, each delivery syringe being capable of holding at least 0.1 ml of ejectable liquid and containing a marking indicating a fill volume of 0.1 ml of ejectable liquid. In systems designed for withdrawal of multiple cefuroxime doses, the vial adapters are preferably swabable, multidose vial adapters. Alternatively, the vial adapter associated with the first perforable vial can be a swabable, multidose vial adapter, and the vial adapter associated with the second perforable vial can be a vented vial adapter. In systems designed for withdrawal of a single cefuroxime dose, vented vial adapters are preferably employed.

Yet another particular embodiment relates to a cefuroxime safety delivery system that comprises (1) a first perforable sterile vial sterile-filled with a measured amount of cefuroxime, (2) a second perforable vial sterile-filled with 0.1 ml of sterile isotonic salt solution per mg cefuroxime in the first perforable vial, a vial-to-vial transfer adapter and a vial adapter with a female luer fitting or one or more shield-protected needles with female luer fitting, and (3) one or more sterilized delivery syringes with male luer fitting, each delivery syringe being capable of holding at least 0.1 ml of ejectable liquid and containing a marking indicating a fill volume of 0.1 ml of ejectable liquid. In systems designed for withdrawal of multiple cefuroxime doses, the vial adapter is preferably a swabable, multidose vial adapter.

A further particular embodiment relates to a cefuroxime safety delivery system that comprises (1) a first perforable sterile vial sterile-filled with a measured amount of cefuroxime, (2) a second perforable vial sterile-filled with 0.1 ml of sterile isotonic salt solution per mg cefuroxime in the first perforable vial and a needleless transfer device, and (3) a sterilized delivery syringe with male luer fitting capable of holding at least 0.1 ml of ejectable liquid and containing a marking indicating a fill volume of 0.1 ml of ejectable liquid.

The subject invention also relates to the use of the latter three particular cefuroxime safety delivery systems for the preparation of one mg doses of cefuroxime for intracameral injection. Preparation of the latter doses comprises the steps of (1) transferring the entire contents of the second perforable vial into the first perforable vial, (2) manually shaking the first perforable vial to obtain a homogenous solution of its contents, and (3) withdrawing into the delivery syringe 0.1 ml of ejectable solution from the first perforable vial.

The invention also relates to simplified cefuroxime safety delivery systems in which a reconstitution syringe (of a capacity of 1 ml or less) doubles as a delivery syringe. In general, these delivery systems comprise (1) a perforable sterile vial sterile-filled with a measured amount of cefuroxime and (2) a receptacle holding 0.1 ml of sterile isotonic salt solution per mg cefuroxime in the perforable vial and means for transferring the isotonic salt solution to the perforable vial and for removing from the perforable vial an aliquot of cefuroxime dissolved in the isotonic salt solution for injection of a volume of 0.1 ml into the eye of a patient.

In a particular embodiment, a delivery system of this type comprises (1) a perforable sterile vial sterile-filled with a measured amount of cefuroxime and (2) a sterile-filled reconstitution syringe with a male luer fitting and containing a marking indicating a fill volume of 0.1 ml of ejectable liquid, the syringe holding 0.1 ml of sterile isotonic salt solution per mg cefuroxime in the perforable vial, and a vial adapter (preferably vented) with a female luer fitting or a shield-protected needle with a female luer fitting.

In another particular embodiment, a delivery system of this type comprises (1) a perforable sterile vial sterile-filled with a measured amount of cefuroxime and (2) a sterile-filled reconstitution syringe with a male luer fitting and containing a marking indicating a fill volume of 0.1 ml of ejectable liquid, the syringe holding 0.1 ml of sterile isotonic salt solution per mg cefuroxime in the perforable vial, and a flow control device.

The subject invention also relates to the use of the above-described particular simplified cefuroxime safety delivery systems for the preparation of one mg doses of cefuroxime for intracameral injection. Preparation of the latter doses comprises the steps of (1) transferring the entire contents of the prefilled reconstitution syringe into the perforable vial comprising cefuroxime, (2) manually shaking said vial to obtain a homogeneous solution of the contents of the closed vial, and (3) withdrawing into the empty reconstitution syringe 0.1 ml of ejectable solution from said vial.

Yet another particular embodiment comprises (1) a first perforable sterile vial sterile-filled with a measured amount of cefuroxime and (2) a second perforable vial sterile-filled with 0.1 ml of sterile isotonic salt solution per mg cefuroxime in the first perforable vial, an empty reconstitution syringe with a male luer fitting, a fill volume sufficiently large to hold the isotonic salt solution contained in the second perforable vial and a marking indicating a fill volume of 0.1 ml of ejectable liquid, and two vial adapters (preferably vented) with female luer fitting or a shield-protected needle with a female luer fitting. In systems in which the cefuroxime solution is being withdrawn through a needle rather than a vial adapter, an additional shield-protected needle with female luer fitting can be included.

The subject invention also relates to the use of the latter cefuroxime safety delivery system for the preparation of a one mg dose of cefuroxime for intracameral injection, the preparation comprising the steps of (1) transferring the entire contents of the second perforable vial into the first perforable vial using the empty reconstitution syringe, (2) manually shaking the first perforable vial to obtain a homogenous solution of its contents, and (3) withdrawing into the empty reconstitution syringe 0.1 ml of ejectable solution from the first perforable vial.

In any of the above-described delivery systems, the perforable vial or the first perforable vial has been powder-filled with cefuroxime under sterile conditions or was sterile-filled with a sterile aqueous solution of cefuroxime, which solution was subjected to lyophilization.

A further delivery system comprises a sterilized two-chamber syringe with a male luer fitting comprising in a first chamber 1 mg of cefuroxime powder and in a second chamber 0.1 ml of water or aqueous solution, the syringe comprising a mechanism for enabling communication between first and second chambers to allow reconstitution of a sterile cefuroxime solution and ejecting the solution.

Another cefuroxime safety delivery system comprises (1) a sterilized two-chamber syringe with a male luer fitting comprising in a first chamber a measured amount of cefuroxime powder and in a second chamber 0.1 ml of isotonic salt solution for every mg of cefuroxime in the first chamber, the syringe comprising a mechanism for enabling communication between first and second chambers to allow reconstitution of a sterile cefuroxime solution and ejecting the solution, (2) a perforable sterile empty vial capable of holding the reconstituted cefuroxime solution from the two-chamber syringe and a vial adapter (preferably a vented vial adapter or, if withdrawal of multiple cefuroxime doses is intended, a swabable multidose vial adapter) with a female luer fitting or one or more shielded sterile needles with female luer fitting and (3) one or more sterilized delivery syringes with male luer fitting, each delivery syringe being capable of holding at least 0.1 ml of ejectable liquid and containing a marking indicating a fill volume of 0.1 ml of ejectable liquid.

A further cefuroxime safety delivery system comprises (1) a sterile cartridge perforably closed at one end, the cartridge comprising two separated chambers of which one contains a measured amount of cefuroxime powder and the other 0.1 ml of sterile isotonic salt solution per mg of cefuroxime, the chambers separated by a divider and the cartridge incorporating a mechanism for displacing the divider to allow communication between the chambers and reconstitution of a cefuroxime solution, (2) one or more sterilized delivery syringes with male luer fitting, each delivery syringe being capable of holding at least 0.1 ml of ejectable liquid and containing a marking indicating a fill volume of 0.1 ml of ejectable liquid, and (3) a vial adapter (preferably a vented vial adapter or, if withdrawal of multiple cefuroxime doses is intended, a swabable, multidose vial adapter) or one or more shielded needles with female luer fitting.

The cefuroxime safety delivery systems of the invention can be packaged in a sealed container, whereby individual or grouped components of the delivery system are sterile-packaged separately. It is implicitly understood that all components of the delivery systems of the invention are provided to the user in a sterile state.

Any of the cefuroxime safety delivery systems of the invention can additionally include user information.

DETAILED DESCRIPTION OF THE INVENTION

As discussed before, there is a well-established medicinal use for cefuroxime in cataract surgery. Ophthalmic practitioners have been using the antibiotic for a period of at least about ten years. The medical benefits of intracameral administration of the antibiotic during cataract surgery were established by large clinical studies. During all of this time, no dosage form of the antibiotic has been developed for ophthalmic use and made available to practitioners, despite the fact that such a dosage form has been demanded in numerous publications. In addition to the references mentioned in the background section, industrial development of a cefuroxime formulation for the eye (mainly for use in cataract surgery) was urged, e.g., in the following publications: Cimberle in Ocular Surgery News, Europe/Asia-Pacific Edition, Jan. 1, 2008; Daly in Eye World, August 2008; Chang in Cataract and Refractive Surgery Today, May 2006; Cimberle in Ocular Surgery News, U.S. Edition, Feb. 1, 2007; Dalton in Eye World, March 2009; Speaker in Cataract and Refractive Surgery Today, May 2009; survey results published in 2009 in J of Cataract and Refractive Surgery 35: 770-773; Chang et al 2007 J of Cataract and Refractive Surgery 33: 1801-05; Young in Eye World, April 2007, September 2009 & March 2010; Barry in Eye World, May 2007; O'hEineachain in Eurotime, November 2006; Barry in Cataract and Refractive Surgery Today, March 2007 & September 2008; Roach in Eyenet, June 2006; Samaniego in 2009 EyeWorld Asia-Pacific, vol. 5, number 2.

There is an inherent danger of contamination as well as of inadvertent use of an unsafe or inappropriate dose of cefuroxime. These potential dangers have long been recognized and were memorialized, e.g., in an editorial written by Garcia-Saenz (Arch Soc Esp Ofthalmol 2006; 81: 569-70). A feature story on cataract surgery by Ursell and colleagues asked for "commercial prepackaged doses of cefuroxime" (Cataract and Refractive Surgery Today Europe, January/February 2007) (see additional references above).

The safety of intracameral administration of 1 mg of cefuroxime in 0.1 ml of aqueous solution has been established (Montan et al 2002 J Cataract Refract Surg 28: 982-7). However, pharmacokinetic analyses suggest that shortly after administration the mean intracameral concentration of cefuroxime is 2.742 mg/ml (Montan et al 2002). This mean concentration drops to 0.756 mg/ml after one hour and is expected to decrease more slowly thereafter. That the safety margin for 1 mg cefuroxime is relatively narrow, i.e., that significant overdosing can be dangerous, is suggested by a study on human corneal endothelial cells showing that 24-hour exposure to cefuroxime at concentrations exceeding 2.75 mg/ml results in a significant reduction in cell viability (Yoeruek et al 2008 J Cataract Refract Surg 34: 2139-45).

The inventors have developed cefuroxime safety delivery systems for ophthalmic use that are optimized based on the following requirements: (1) The safety delivery system needs to be a "closed system" so that sterility can be guaranteed. (2) The safety delivery system needs to allow the user to conveniently and reliably prepare a correct dose of cefuroxime for intracameral injection. (3) Use must be simple and only involve a minimal number of steps so that the possibility of mistakes by the user is reduced to a minimum. Use of the delivery system should also reduce the systematic error inherent in the preparation of an adequate cefuroxime dose by a hospital pharmacy or a practitioner. (4) Use of the delivery system should result in a shortening of the time of preparation of a cefuroxime dose compared with current practice; as a consequence, the overall time required for a cataract surgery should be reduced. (5) The delivery system should be relatively inexpensive to encourage practitioners to make use of it, thereby enhancing the safety of cefuroxime preventative therapy. The availability of an inexpensive delivery system is also expected to convince practitioners that have not used intracameral cefuroxime before to include the antibiotic in their cataract or other ophthalmic procedures with the expected benefit of further reducing the incidence of endophthalmitis.

A preferred delivery system of the invention comprises, typically in a sealed container, (1) a perforable sterile vial containing a measured amount of sterile-filled cefuroxime, (2) a syringe having a male luer fitting sterile-filled with an isotonic salt solution, typically 0.1 ml for every 1 mg of cefuroxime in the perforable vial, for dissolving the cefuroxime in the perforable sterile vial (reconstitution syringe), (3) a vial adapter with female luer fitting and (4) one or more syringes (delivery syringes) with male luer fitting for intracameral administration of an appropriate dose of cefuroxime. Typically, the appropriate dose of cefuroxime to be administered is one mg. The delivery system can further comprise one or more shielded injection needles. Alternatively, and this applies mutatis mutandis to other delivery systems of the invention, the perforable sterile vial can comprise a measured amount of cefuroxime in combination with an adequate amount of salt to generate an isotonic solution upon reconstitution (typically to a cefuroxime concentration of 10 mg/ml and a concentration of NaCl of 9 mg/ml) and a reconstitution syringe prefilled with water (water for injection). The vial adapter is characterized by having two sides, of which one contains a port comprising a female luer fitting (or luer lock) and the other is capable of fitting over the perforable vial, penetrating the septum of the perforable vial and thereby providing a path for adding to the perforable vial a volume of liquid contained in a syringe connected to the latter port or withdrawing a volume contained in the perforable vial into such syringe. Vial adapters of this kind that may be vented or designed for multiuse are commercially available, e.g., from West Pharmaceutical Services, Inc., Lionville, Pa., Bioject Medical Technologies Inc., Tualatin, Oreg., Baxa Corp, Englewood, Colo. If multiple delivery syringes are provided, i.e., if multiple aliquots or doses of cefuroxime solution are to be withdrawn, a multiuse vial adapter secured by a valve is preferably employed (e.g., the swabable vial adapter from West). Prefilled syringes can be obtained from a variety of sources including from Vetter Pharma International GmbH, Ravensburg, Germany, Gerresheimer Bünde, Bünde, Germany, Beckton Dickinson, Franklin Lakes, N.J. (e.g., BD Hypak PRTC and SCF systems), Baxter Healthcare Corp., Round Lake, Ill., and Sewa Medicals Ltd., Mumbai, India. Suitable delivery syringes can be obtained from various manufacturers, including, e.g., "Sol-Ject Auto-Disable" 0.1 or 0.5 ml syringes from Zhejiang Sol-Millennium Plastic, Zhejiang, PR, Gerresheimer Bünde, Bünde, Germany ("ClearJect"). If not already provided as component of a delivery system of the invention, the practitioner can select his/her preferred injection needle. Example injection needles include Anterior Chamber Cannulas from Rycroft that are distributed, e.g., by Rumex International Co. St. Petersburg, Fla. Example prefilled syringes were described in U.S. Pat. Nos. 5,833,653, 7,041,087, 7,331,941 and 7,645,267. Examples vial adapters are described in U.S. Pat. No. 7,326,194). Whenever luer fittings are mentioned in the subject application, these fitting can be luer locks of luer-slip fittings. Unless a specific amount is indicated, the amount of dry cefuroxime in the perforable vial (or first perforable vial) of any delivery system of the invention can be any amount from one mg to about 100 mg. A user of the latter preferred delivery system will first mount the vial adapter on the cefuroxime-containing vial and join the prefilled reconstitution syringe to the port of the vial adapter. By advancing the plunger of the reconstitutinon syringe, the user will inject the entire contents of the syringe into the latter vial. The user will then disengage the reconstitution syringe and completely dissolve the cefuroxime by gentle agitation of the adapter-containing vial. He/she will then mount a delivery syringe to the port of the vial adapter. With the vial in an inverted position, the plunger of the delivery syringe will be retracted by the user to withdraw into the syringe an adequate volume (typically >0.1 ml) of reconstituted cefuroxime solution. The user will subsequently disengage the delivery syringe from the adapter, add the injection needle of choice to the syringe, and inject, typically, 0.1 ml of the cefuroxime solution into the eye of a patient.

In another embodiment of the above-described preferred delivery system (referred to below as the first-described preferred delivery system), the prefilled reconstitution syringe is replaced by a second perforable sterile vial sterile-filled with isotonic salt solution, a second vial adapter and an unfilled reconstitution syringe, for example a Oneject auto-disable syringe from PT Oneject Indonesia, Bogor, Indonesia (available for capacities between 0.5 ml and 5 ml). The two vial adapters are preferably vented vial adapters. If the system is intended to provide multiple cefuroxime doses, at least the adapter that is to be mounted on the first perforable vial containing cefuroxime preferably will be a swabable multiuse vial adapter. To facilitate operation, both adapters can be swabable multiuse vial adapters. The operation of this delivery system is very similar to that of the above-described preferred delivery system, except for the additional step of filling the reconstitution syringe from the vial containing the isotonic salt solution.

In yet another embodiment of the first-described preferred delivery system, the prefilled reconstitution syringe is replaced by a second perforable sterile vial sterile-filled with isotonic salt solution and a vial-to-vial transfer adapter. A suitable vial-to-vial transfer adapter is marketed by West under the name Mix2Vial. U.S. Pat. Nos. 6,558,365 and 6,699,229. The user of this delivery system will join first and second perforable vials by means of the vial-to-vial transfer adapter and transfer the salt solution in the second perforable vial into the cefuroxime-containing first perforable vial. The assembly will be agitated manually to obtain a homogenous solution of cefuroxime. Thereafter, the vial containing the cefuroxime solution will be disengaged. The vial adapter will then be mounted onto the latter vial and a delivery syringe joined to the adapter. An appropriate volume of cefuroxime solution will then be withdrawn into the delivery syringe as before.

In a further embodiment, both the prefilled reconstitution syringe and the vial adapter of the first-described preferred delivery system (elements 2 and 3) are replaced by a second perforable sterile vial sterile-filled with isotonic salt solution and a needleless transfer device. Such a device is marketed by West and is the subject of U.S. Pat. No. 6,379,340. A user of this delivery system will join the first and second perforable vials to the needleless transfer device to transfer the salt solution of the second perforable vial to the cefuroxime-containing first perforable vial. After gently agitating the assembly, a delivery syringe will be docked to the single needle port (female luer fitting) of the needleless transfer device, and an adequate volume of cefuroxime solution will be withdrawn into the delivery syringe for injection into the eye of a patient.

Another embodiment of the delivery system of the invention comprises, typically in a sealed container, (1) a perforable sterile vial containing a measured amount of sterile-filled cefuroxime, (2) a syringe comprising a male luer fitting, the syringe sterile-filled with an isotonic salt solution, typically 0.1 ml for every 1 mg of cefuroxime in the perforable vial, for dissolving the cefuroxime in the perforable sterile vial (reconstitution syringe), (3) a flow control device and (4) a syringe (delivery syringe) with male luer fitting for intracameral administration of an appropriate dose of cefuroxime. The delivery system can further comprise a shielded injection needle that is either already mounted on the flow control device or provided separately. Flow control devices are described, e.g., in U.S. Pat. Nos. 6,379,340 and 6,238,372. Flow control devices of the type disclosed in the latter patents are commercialized under the trade name MixJect by West Pharmaceutical Service Inc. U.S. Pat. No. 7,326,194. These flow control devices have three ports, a first port (with female luer fitting) for a prefilled syringe, a second port (with male luer fitting) for an injection needle and a third port adapted to fit over the top of a vial and capable of penetrating the septum or stopper of the vial and creating an open path. A user of this delivery system will connect the prefilled reconstitution syringe to the first port of the flow control device as well as mount the cefuroxime-containing vial to the third port. By advancing the plunger of the reconstitution syringe, the user will inject the entire contents of the syringe into the latter vial. The cefuroxime solution is then reconstituted by gentle agitation of the assembly. The user then replaces the reconstitution syringe with a delivery syringe. With the vial in an inverted position, the plunger is retracted to withdraw an appropriate volume of cefuroxime solution into the syringe body (typically >0.1 ml to ensure an ejectable volume of 0.1 ml). Subsequent to the removal of the vial, and mounting of the injection needle (if not mounted already), forward movement of the plunger of the delivery syringe will cause the cefuroxime solution to be ejected through the needle.

When reconstitution syringes are used that have a capacity of one ml or less, the preferred delivery systems can be further simplified. A simplified preferred delivery system of the invention comprises, typically in a sealed container, (1) a perforable sterile vial containing a measured amount of sterile-filled cefuroxime, (2) a syringe having a male luer fitting and a marking indicating a 0.1 ml fill volume that is sterile-filled with an isotonic salt solution, typically 0.1 ml for every 1 mg of cefuroxime in the perforable vial, for dissolving the cefuroxime in the perforable sterile vial (reconstitution syringe) and (3) a vial adapter having a female luer fitting. The delivery system can further comprise a shielded needle for injection into the eye, which needle is to be mounted on the reconstitution syringe. A user of this delivery system will first mount the vial adapter on the cefuroxime-containing vial and dock the reconstitution syringe to the port of the vial adapter. By advancing the plunger of the reconstitution syringe, the user will inject the entire contents of the syringe into the latter vial. The user will then reconstitute the cefuroxime solution by gentle agitation of the entire assembly. With the vial in an inverted position, the plunger of the reconstitution syringe will be retracted by the user to withdraw into the syringe an adequate volume (>0.1 ml) of reconstituted cefuroxime solution. The user will subsequently disengage the syringe from the adapter, add the injection needle, and inject a volume comprising 1 mg of cefuroxime (typically, 0.1 ml) of the cefuroxime solution into the eye of a patient.

Another simplified preferred delivery system of the invention comprises, typically in a sealed container, (1) a perforable sterile vial containing a measured amount of sterile-filled cefuroxime, (2) a syringe having a male luer fitting and a marking indicating a 0.1 ml fill volume, the syringe sterile-filled with an isotonic salt solution, typically 0.1 ml for every 1 mg of cefuroxime in the perforable vial, for dissolving the cefuroxime in the perforable sterile vial (reconstitution syringe) and (3) a flow control device, preferably a MixJect device from West. The delivery system can further comprise a shielded needle for injection into the eye. A user of a delivery system of this kind that incorporates, a MixJect device will introduce the cefuroxime-containing vial into the third port of the flow control device and connect the prefilled reconstitution syringe to the first port. By advancing the plunger of the reconstitution syringe, the user will inject the entire contents of the syringe into the latter vial. The cefuroxime solution will be reconstituted by gentle agitation of the entire assembly. With the vial in an inverted position, the plunger of the syringe will be retracted to withdraw an appropriate volume of cefuroxime solution into the syringe body (>0.1 ml). Subsequent to the removal of the vial and the mounting of the injection needle, forward movement of the plunger of the syringe will cause the cefuroxime solution to be ejected through the needle.

In another embodiment, a delivery system of the invention comprises, typically in a sealed container, (1) a perforable sterile vial containing a measured amount of sterile-filled cefuroxime, (2) a syringe having a male luer fitting, the syringe sterile-filled with an isotonic salt solution, typically 0.1 ml for every 1 mg of cefuroxime in the perforable vial, for dissolving the cefuroxime in the perforable sterile vial (reconstitution syringe) and a shielded needle with a female luer fitting already mounted on the reconstitution syringe or provided separately, and (3) one or more syringes (delivery syringes) comprising a male luer fitting and, typically, containing a marking indicating a 0.1 ml fill volume for intracameral administration of an appropriate dose of cefuroxime. The delivery system can include one or more additional needles with a female luer fitting that are mounted one the one or more delivery syringes or provided separately. When a reconstitution syringe is used that has a capacity of one ml or less, the delivery system can be further simplified. Such a simplified delivery system comprises, typically in a sealed container, (1) a perforable sterile vial containing a measured amount of sterile-filled cefuroxime and (2) a syringe comprising a male luer fitting and a marking indicating a 0.1 ml fill volume, the syringe sterile-filled with an isotonic salt solution, typically 0.1 ml for every 1 mg of cefuroxime in the perforable vial, for dissolving the cefuroxime in the perforable sterile vial (reconstitution syringe) and a shielded needle with a female luer fitting already mounted on the reconstitution syringe or provided separately. The latter needle is, typically, straight, which is not the shape of an anterior chamber injection needle or cannula preferred by many practitioners. The delivery system, therefore, can further comprise a shielded dedicated injection needle that is to be mounted on the reconstitution syringe for injection of cefuroxime solution into the eye of a patient. A user of the latter simplified delivery system will inject the prefilled contents of the reconstitution syringe (fitted with a needle) into the cefuroxime vial, agitate the vial to fully dissolve the cefuroxime and withdraw an appropriate volume of cefuroxime solution into the reconstitution syringe. The needle on the reconstitution syringe can then be replaced with the injection needle, and a correct dose of cefuroxime (typically, 0.1 ml) is injected into the eye of a patient.

A typical process for preparing perforable sterile vials containing a measured amount of cefuroxime ($C_{16}H_{16}N_4O_8S$; CAS number 55268-75-2; available from GlaxoSmithKline Ltd.) and salt is as follows: a bulk solution of, e.g., 120 liters, is prepared that contains 10 mg/ml cefuroxime and 0.9% sodium chloride in water purified by distillation or reverse osmosis (water for injection). This solution is passed through one or more sterile filters, the last typically having a pore size of about 0.2 micrometer, and appropriately sized, sterile vials are sterile-filled with 0.5 ml of the filtered cefuroxime solution (batch size of 200,000 vials). The cefuroxime solution in the vials is lyophilized overnight under sterile conditions. Finally, the vials or ampoules (terms used interchangeably) are capped. Different types of perforable ampoules can be utilized. Typically used are crimp top vials that are closed by means of a crimp top seal containing a septum. To avoid surface discoloration of the cefuroxime powder, colored (e.g., amber) or darkly surface-coated vials or ampoules are preferred over clear glass vials or ampoules. It is noted that, if the liquid in the reconstitution syringe is an isotonic salt solution, vials are sterile-filled with a solution of cefuroxime in water. It is further noted that the concentration of cefuroxime in the filling solution does not need to be 10 mg/ml. Depending on sterile-filling equipment available, any concentration of up to 20% w/v in water can be used. The present invention is not limited by any particular method for preparing vials or ampoules containing a measured amount of dry cefuroxime. Instead of delivery of an aqueous solution containing cefuroxime followed by lyophilization, vials may be powder-filled using microjets that are capable of controlling the amount of powder delivered (e.g., the "Omnidose" microdosing system of Harro Hoefliger, Allmersbach im Tal, Germany). Particularly suitable for aseptic powder-filling of cefuroxime are the MICROFILL high speed microdosing machines, in particular the MICROFILL SERIES 400 machines, from I.M.A. (Industria Macchine Automatiche) S.p.A, Bologna, Italy. A possible further approach would entail sterile-filling vials with a solution of cefuroxime in dimethyl sulfoxide (up to 10% w/v).

To prepare a cefuroxime solution for injection into an eye of a patient, the entire volume of liquid contained in the reconstitution syringe (or a second perforable vial) is transferred to the cefuroxime-containing (perforable or first perforable) vial, and the vial is manually agitated to obtain a homogeneous solution of cefuroxime. Preferably, the antibiotic will be present in the vial at a concentration of 10 mg/ml. In preferred examples, the (first) perforable vial contains 50-100 mg of cefuroxime, and the reconstitution syringe or second perforable vial contains 5-10 ml of isotonic salt solution, the volume of salt solution adjusted to the amount of cefuroxime so that a solution containing 10 mg/ml cefuroxime results. An aliquot of the cefuroxime solution is then withdrawn from the vial into a delivery syringe properly dimensioned for receiving the aliquot. Preferred is a delivery syringe with an ejectable volume of 0.1 ml. The entire volume of cefuroxime solution contained in the delivery syringe is injected intracamerally at the end of a cataract procedure or other ophthalmic surgery. It is noted that the delivery syringe preferably incorporates an auto-disabling mechanism to ensure that the syringe can only be utilized for a single injection procedure, thereby reducing the risk of contamination inherent in repeated uses of a syringe. The delivery syringe can also feature a piston stopper. While an auto-disabling feature does not appear to be critical for the reconstitution syringe, embodiments of the delivery systems of the invention may also comprise an auto-disabled reconstitution syringe. It is noted that a delivery syringe with a larger ejectable volume can be used (up to about 1 ml), provided that it contains a marking indicating a 0.1 ml fill volume. It is further noted that in simplified versions of the delivery systems of the invention the reconstitution syringe also doubles as the delivery syringe. For obvious reasons, the reconstitution syringe in such delivery systems will not comprise an auto-disabling mechanism.

The components of the delivery system are presented in an appropriate sealed container typically made from thermoplastic material. Packaging of the delivery system components into such container may occur under sterile or clean conditions using methods and procedures well known in the art. User instructions are provided on an outer packaging, added inside the outer packaging, printed on the sealed container containing the delivery system, or added inside the container. User instructions may be displayed more than once. Certain embodiments of the delivery system contain multiple delivery syringes. A single (preferably autodisabled) delivery syringe per delivery system is preferred in the interest of keeping risk of contamination to a minimum.

In the above-described embodiments of delivery systems of the invention, the cefuroxime in the perforable vial is dissolved to a concentration of 10 mg/ml, and a volume of 0.1 ml is injected in the eye to deposit the desired amount of 1 mg cefuroxime in the eye. It will be clear to a skilled artisan that equivalent or nearly equivalent delivery systems can be produced, in which cefuroxime in the perforable vial is dissolved to a different concentration, provided that the necessary compensation in the volume injected in the eye is made so that 1 mg of drug substance is deposited. For example, if a reconstitution syringe containing 1 ml of isotonic salt solution were used to dissolve a 5 mg quantity of cefuroxime, a delivery syringe would be associated that is capable of delivering a volume of 0.2 ml of cefuroxime solution to the eye. Such equivalent delivery systems are considered to be within the scope of the present invention. The latter considerations also apply to equivalent or alternative delivery systems described hereinafter.

The safety delivery systems are "closed" systems in the interest of ensuring sterility until the time of use. The (sterilized) components of the delivery system are assembled and packaged in a sealed container. Although this is not required, the latter assembly and packaging can be performed under sterile conditions. Such sterile assembly makes sterile-packaging of the various components optional. If assembly and packaging in the sealed container is not performed under sterile conditions, delivery system components are individually sterile-packaged, e.g., in blister packs.

The safety delivery systems allow the user to conveniently and reliably prepare an appropriate dose of cefuroxime for intracameral injection. An appropriate dose is 1 mg cefuroxime as used in the large clinical studies referenced above. Besides the removal of protective packaging, covers and needle shields and assembly of components, preparation of an appropriate dose of cefuroxime using a delivery system of the invention involves three simple steps. The first step is introduction of the entire volume of the isotonic salt solution contained in a prefilled reconstitution syringe or a second perforable vial though the septum or stopper of a cefuroxime-containing first perforable vial. Step two involves manual shaking of the latter vial for a prescribed number of times resulting in a homogeneous solution of cefuroxime. The final step is filling of the delivery syringe (or emptied reconstitution syringe as the case may be) with a prescribed volume of cefuroxime solution from the cefuroxime-containing vial.

Use of the safety delivery systems greatly reduces the possibility of significant user error. The volume of liquid contained in the reconstitution syringe (or second perforable vial) is that required for preparing a 10 mg/ml cefuroxime solution in the drug-containing vial. Hence, the user only needs to empty the reconstitution syringe or second perforable vial into the cefuroxime-containing vial. Errors in reading graduations that could occur, if only a fraction of the liquid was to be transferred, are avoided. The delivery syringe (or reconstitution syringe in simplified delivery systems) is so marked that significant accidental overfilling due to misreading of a graduation should not occur. Ideally, the dimension of the delivery syringe is such that essentially the entire contents of the delivery syringe will have to be injected into the eye (in order to deposit 1 mg of cefuroxime). In any case, at most a single graduation on the delivery syringe (or reconstitution syringe in simplified delivery systems) needs to be identified by the practitioner preparing for an injection of a correct drug dose into the eye of a patient.

The delivery systems significantly reduce the errors inherent in the preparation of an appropriate cefuroxime dose by a hospital pharmacy or a practitioner. As mentioned previously, the protocol used in the ESCRS study for preparing an appropriate cefuroxime dose encompassed 16 different steps. There is a possibility for accidental errors (mistakes of preparer) and systemic errors (small errors due to unavoidable inaccuracies) at 8 of these steps. Assuming that the amount of cefuroxime in the drug-containing vial and the volume of liquid in the prefilled reconstitution syringe (or diluent-containing vial) are correct (as a result of quality control by the manufacturer), there may be only 2 steps at which accidental errors can be made when using the delivery system for preparing a cefuroxime dose. A systemic error may only occur at one step. Hence, use of the delivery systems should dramatically reduce accidental and systemic errors that affect the cefuroxime dose delivered to the eye and, therefore, is expected to increase the safety of the prophylactic regimen.

Handling of the delivery systems is simple compared to the preparation of an appropriate cefuroxime dose by a practitioner or his laboratory or pharmacy. As discussed above, the 16 steps prescribed by the ESCRS study are replaced in the delivery systems by the removal of protective packaging, covers and needle shields and assembly of components, and three easy manipulations. This substantial decrease in complexity of manipulations will reduce the workload of the practitioner and/or eliminate the need for coordinated pharmacy activity. The availability of a safety delivery system for cefuroxime in the marketplace will also lead practitioners who have not used cefuroxime before, be it because of the inconvenience of custom preparation of appropriate doses or because of concerns about possible mistakes that may happen during such custom preparation of cefuroxime doses, to make use of this prophylactic regimen that has been proven to reduce the occurrence of endophthalmitis.

A cefuroxime safety delivery system should be inexpensive to produce. The lower the price of a delivery system, the greater will be the likelihood that practitioners will make use of it instead of foregoing cefuroxime prophylaxis or preparing cefuroxime doses themselves with the attendant risk of errors and the possible dangers of contamination and overdosing (danger of cytotoxic effects) or underdosing (lack of efficacy; danger of enhancing the development of bacterial resistance) the patient. Several of the above-described preferred delivery systems represent low-cost as well as efficient solutions, because their components are comparatively simple to manufacture as well as are readily available from suppliers.

Other solutions to the problem of assembling an optimal cefuroxime safety delivery system are provided below. However, primarily because they incorporate more complex and, therefore, generally more expensive technology, these delivery systems may be less cost-effective than the aforedescribed delivery systems. For example, use can be made of a two-chamber or mixing syringe. Such syringes are capable of holding dry cefuroxime or cefuroxime in one chamber and diluent, i.e., isotonic salt solution, in the other chamber, and of being triggered to mix the contents of the two chambers to produce a desired cefuroxime solution. Example two-chamber syringes were described in U.S. Pat. Nos. 3,327,710; 3,380,451; 4,581,016; 4,874,381; 5,779,668; 6,419,656; 6,770,052 and 6,817,987; U.S. reexamined Pat. No. 35986; European Patent Application No. 112574. Two-chamber syringes with male luer fitting can be obtained from several sources, including from Vetter Pharma (LyoJect®). In particular, a safety delivery system for administering the desired dose of cefuroxime (1 mg) to an eye of a patient can comprise a two-chamber syringe sterile-filled with 1 mg of cefuroxime and containing in the second chamber 0.1 ml of isotonic salt solution. (Dead volume can be compensated by slightly overfilling the syringe.) The syringe can be packaged, in a clean or sterile fashion, in a container as described before for the preferred safety delivery systems. User instructions can also be provided with the delivery system. As with the earlier-described delivery systems, this delivery system can also include a shielded injection needle with a female luer fitting.

A similar safety delivery system comprises a two-chamber syringe with male luer fitting, a perforable empty sterile vial or ampoule capable of holding at least as much liquid as the two-chamber syringe and one or more 0.1-ml delivery syringes with male luer fitting. A vial adapter or shielded sterile needle, with female luer fitting, is also provided for transferring liquid to and from the sterile vial. The two-chamber syringe contains, e.g., 5 mg of dry cefuroxime in one chamber and 0.5 ml of ejectable isotonic salt solution in the other chamber. Upon activation of the syringe mechanism, the contents of the two chambers are mixed, and the resulting isotonic cefuroxime solution can be transferred to the empty sterile vial. One or more delivery syringes can be filled with 0.1 ml of ejectable cefuroxime solution from the latter vial. The delivery system can be packaged, in a clean or sterile fashion, in a container as described before for the preferred safety delivery system. User instructions can also be provided with the delivery system. Especially, if it is intended to provide multiple cefuroxime doses, the delivery system contains a multiuse vial adapter. Systems not making use of a vial adapter can include one or more additional shielded needles with female luer fitting (for withdrawing cefuroxime solution from the vial).

In another embodiment, the safety delivery system comprises a two-chamber perforable vial. One of the chambers is sterile-filled with cefuroxime powder (e.g., 5 mg), whereas the other chamber holds an appropriate volume of isotonic salt solution (e.g., 0.5 ml). Incorporated in the vial is a mechanism that upon actuation releases the salt solution into the dry cefuroxime-containing chamber for reconstitution. Subsequent to manual agitation for obtaining a homogeneous cefuroxime solution, a delivery syringe(s) would be used to withdraw 0.1 ml of cefuroxime solution, representing a single dose for intracameral injection. A vial adapter (preferably with a valve) or a shielded needle(s) will be needed for the latter withdrawal of cefuroxime solution into the delivery syringe(s). Suitable two-chamber vial or cartridge systems are commercially available, e.g., Act-O-Vial from Pfizer CentreSource (Kalamazoo, Mich.) and "EZ Fusion two-in-one" by Degill International Corp. of Taiwan. To list its components, the delivery system includes a two-chamber vial or cartridge containing cefuroxime and isotonic salt solution, one or more 0.1-ml sterile delivery syringes with male luer fitting and a vial adapter or one or more needles with female luer fitting for withdrawing liquid from the vial into the delivery syringe(s). The delivery system will be assembled and packaged in a container and contain user information as described before for the preferred safety delivery systems. The delivery system can also include one or more shielded injection needles with female luer fitting.

Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context). Reference to a "means" can optionally be characterized as one or more devices.

This invention includes all modifications and equivalents of the subject matter recited in the aspects or claims presented herein to the maximum extent permitted by applicable law.

The invention claimed is:

1. Cefuroxime safety delivery system, comprising
   (a) A perforable sterile vial sterile-filled with a measured amount of cefuroxime,
   (b) A receptacle holding 0.1 ml of sterile isotonic salt solution per mg cefuroxime in the perforable vial and means for transferring the isotonic salt solution to the perforable vial and for removing from the perforable vial an aliquot of cefuroxime dissolved in the isotonic salt solution into a delivery syringe, and
   (c) one or more sterilized delivery syringes with male luer fitting, each delivery syringe of the one or more sterilized delivery syringes being capable of holding at least 0.1 ml of ejectable liquid and containing a marking indicating a fill volume of 0.1 ml of ejectable liquid.

2. The cefuroxime safety delivery system according to claim 1 wherein the receptacle is a sterile-filled reconstitution syringe with a male luer fitting and the means for transferring the isotonic salt solution to the perforable vial and for removing from the perforable vial an aliquot of cefuroxime dissolved in the isotonic salt solution into the delivery syringe is a vial adapter with a female luer fitting or one or more needles with a female luer fitting.

3. The cefuroxime safety delivery system according to claim 1 wherein the receptacle is a sterile-filled reconstitution syringe with a male luer fitting and the means for transferring the isotonic salt solution to the perforable vial and for removing from the perforable vial an aliquot of cefuroxime dissolved in the isotonic salt solution into the delivery syringe is a flow control device.

4. The cefuroxime safety delivery system of claim 3, wherein a sterile filter is mounted on the delivery syringe to remove fine particles from the aliquot of cefuroxime dissolved in the isotonic salt solution in the delivery syringe.

5. The cefuroxime safety delivery system according to claim 1 wherein the receptacle is a perforable sterile vial sterile-filled with the isotonic salt solution, and the means for transferring the isotonic salt solution to the perforable sterile vial sterile-filled with a measured amount of cefuroxime and for removing from the latter perforable vial an aliquot of cefuroxime dissolved in the isotonic salt solution into the delivery syringe is an empty reconstitution syringe with a male luer fitting and a fill volume sufficiently large to hold the isotonic salt solution contained in the receptacle and two vial adapters with female luer fitting or one or more shield-protected needles with female luer fitting.

6. The cefuroxime safety delivery system according to claim 1 wherein the receptacle is a perforable sterile vial sterile-filled with the isotonic salt solution, and the means for transferring the isotonic salt solution to the perforable sterile vial sterile-filled with a measured amount of cefuroxime and for removing from the latter perforable vial an aliquot of cefuroxime dissolved in the isotonic salt solution into the delivery syringe is a vial-to-vial transfer adapter and a vial adapter with a female luer fitting or one or more shield-protected needles with female luer fitting.

7. The cefuroxime safety delivery system according to claim 1 wherein the receptacle is a perforable sterile vial sterile-filled with the isotonic salt solution, and the means for transferring the isotonic salt solution to the perforable sterile vial sterile-filled with a measured amount of cefuroxime and for removing from the latter perforable vial an aliquot of cefuroxime dissolved in the isotonic salt solution into the delivery syringe is a needleless transfer device.

8. The cefuroxime safety delivery system according to claim 1 wherein the perforable vial has been powder-filled with cefuroxime under sterile conditions or was sterile-filled with a sterile aqueous solution of cefuroxime, which solution was subjected to lyophilization.

9. The cefuroxime safety delivery system of claim 1 packaged in a sealed container, whereby individual or grouped components of the cefuroxime safety delivery system are sterile-packaged separately.

10. The cefuroxime safety delivery system of claim 1, the cefuroxime safety delivery system further including user information.

11. The cefuroxime safety delivery system of claim 1, wherein a sterile filter is mounted on the delivery syringe to remove fine particles from the aliquot of cefuroxime dissolved in the isotonic salt solution in the delivery syringe.

12. Cefuroxime safety delivery system, comprising
    (a) a perforable sterile vial sterile-filled with a measured amount of cefuroxime, and
    (b) a reconstitution syringe sterile-filled with 0.1 ml of sterile isotonic salt solution per mg cefuroxime in the perforable vial, the reconstitution syringe having a male luer fitting and containing a marking indicating a fill volume of 0.1 ml of ejectable liquid, and means for transferring the isotonic salt solution from the sterile-filled reconstitution syringe to the perforable vial and for removing from the perforable vial an aliquot of cefuroxime dissolved in the isotonic salt solution into the emptied reconstitution syringe for injection of a volume of 0.1 ml into the eye of a patient.

13. The cefuroxime safety delivery system according to claim 12 wherein the means for transferring the Isotonic salt solution from the sterile-filled reconstitution syringe to the perforable vial and for removing from the perforable vial an aliquot of cefuroxime dissolved in the isotonic salt solution into the emptied reconstitution syringe for injection of a volume of 0.1 ml into the eye of a patient consists of a vial adapter with a female luer fitting or a shield-protected needle with a female luer fitting.

14. The cefuroxime safety delivery system according to claim 12 wherein the means for transferring the isotonic salt solution from the sterile-filled reconstitution syringe to the perforable vial and for removing from the perforable vial an aliquot of cefuroxime dissolved in the isotonic salt solution into the emptied reconstitution syringe for injection of a volume of 0.1 ml into the eye of a patient consists of a flow control device.

15. The cefuroxime safety delivery system according to claim 12 wherein the perforable vial has been powder-filled with cefuroxime under sterile conditions or was sterile-filled with a sterile aqueous solution of cefuroxime, which solution was subjected to lyophilization.

16. The cefuroxime safety delivery system of claim 12 packaged in a sealed container, whereby individual or grouped components of the cefuroxime safety delivery system are sterile-packaged separately.

17. The cefuroxime safety delivery system of claim 12, the cefuroxime safety delivery system further including user information.

18. Cefuroxime safety delivery system, comprising
    (a) a first perforable sterile vial sterile-filled with a measured amount of cefuroxime,
    (b) a second perforable vial sterile-filled with 0.1 ml of sterile isotonic salt solution per mg cefuroxime in the first perforable vial and
    (c) means for transferring the isotonic salt solution from the second perforable vial to the first perforable vial and for removing from the first perforable vial an aliquot of cefuroxime dissolved in the isotonic salt solution for injection of a volume of 0.1 ml into the eye of a patient, the means consisting of an empty reconstitution syringe with a male luer rating, a fill volume sufficiently large to hold the isotonic salt solution contained in the second perforable vial and a marking indicating a fill volume of 0.1 ml of ejectable liquid, and two vial adapters with female luer fitting or a shield-protected needle with a female luer fitting.

19. The cefuroxime safety delivery system according to claim 18 wherein the first perforable vial has been powder-filled with cefuroxime under sterile conditions or was sterile-filled with a sterile aqueous solution of cefuroxime, which solution was subjected to lyophilization.

20. The cefuroxime safety delivery system of claim 18 packaged in a sealed container, whereby individual or grouped components of the cefuroxime safety delivery system are sterile-packaged separately.

21. The cefuroxime safety delivery system of claim 18, the cefuroxime safety delivery system further including user information.

* * * * *